US006274581B1

(12) United States Patent
Gross (10) Patent No.: US 6,274,581 B1
(45) Date of Patent: *Aug. 14, 2001

(54) BLOCKING INDUCTION OF TETRAHYDROBIOPTERIN TO BLOCK INDUCTION OF NITRIC OXIDE SYNTHESIS

(75) Inventor: Steven S. Gross, New York, NY (US)

(73) Assignee: Cornell Research Foundation, Inc., Ithaca, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 08/063,067

(22) Filed: May 20, 1993

Related U.S. Application Data

(63) Continuation of application No. 07/813,507, filed on Dec. 26, 1991, now abandoned.

(51) Int. Cl.[7] .......................... A61K 31/495; A61K 31/50
(52) U.S. Cl. ............................................. 514/249
(58) Field of Search ............................................. 514/249

(56) References Cited

U.S. PATENT DOCUMENTS

| | | | |
|---|---|---|---|
| 3,557,106 | 1/1971 | Roch | 544/260 X |
| 4,282,217 | 8/1981 | Baglioni et al. . | |
| 4,670,438 | * 6/1987 | Austel et al. | 514/249 |
| 4,701,455 | * 10/1987 | Nichol et al. | 514/249 |
| 4,734,438 | 3/1988 | Macri | 514/653 |
| 5,002,944 | * 3/1991 | Spada | 514/221 |
| 5,028,627 | 7/1991 | Kilbourn et al. . | |
| 5,059,712 | 10/1991 | Griffith . | |

FOREIGN PATENT DOCUMENTS

| | | | |
|---|---|---|---|
| 8404040 | * 10/1984 | (EP) | A61K/31/505 |
| PCT/US90/ 05199 | 9/1990 | (WO) . | |

OTHER PUBLICATIONS

Rees et al 110 CA:112347q 1989.*
Salvemini et al. 115 CA 204139c 1991.*
Kwon et al 111 CA 230525 q 1989.*
Med Index 10th Ed #1227 & 7834.*
Collier, J., et al, Trends in Pharmacological Sciences Including Toxicological Sciences, Elsevier Science Publishers, Ltd., published in UK, 1989, front page and pp. 428–431.
Marletta, M.A., "Nitric oxide: biosynthesis and biological significance", name of publication unknown, Elsevier Science Publishers, Ltd. (UK), pp. 448–453 (1989).
Moncada, S., et al, Pharmacological Reviews 43(2):109–142 (1991).
Werner, E., et al, Biochem. J., 262:861–866(1989).
Stuehr, D.J. et al, Synthesis of Nitrogen Oxides from L–Arginine by Macrophage Cytosol: Requirement for Inducible and Constitutive Components, Biochem, Biophys. Res. Commun., (1989) vol. 161, 420–426.

Stuehr, D.J. et al., Activated Murine Macrophages Secrete a Metabolite of Arginine with the Bioactivity of Endothelium–Derived Relaxing Factor and the Chemical Reactivity of Nitric Oxide, J. Exp. Med., (1989) vol. 169, 1011–1020.
Rees, D.D. et al., Role of Endothelium–Derived Nitric Oxide in the Regulation of Blood Pressure, Proc. Natl. Acad. Sci. U.S.A., (1989) vol. 86, 3375–3378.
Aisaka, K. et al., $N^G$–Methylarginine, An Inhibitor of Endothelium–Derived Nitric Oxide Synthesis, is a Potent Pressor Agent in the Guinea Pig: Does Nitric Oxide Regulate Blood Pressure in vivo, Biochem. Biophys. Res. Commun. (1989) 160:881–886.
Natanson, C. et al., Endotoxin and Tumor Necrosis Factor Challenges in Dogs Simulate the Cardiovascular Profile of Human Septic Shock, Journal of Exp. Med. (1989) 169:823–832.
Schmidt, H. et al., Arginine is a Physiological Precursor of Endothelium–Derived Nitric Oxide, Eur. J. of Pharmacology (1988) 154:213–216.
Palmer, R.M.J. et al., L–Arginine is the Physiological Precursor for the formation of Nitric Oxide in Endothelium–Dependent Relaxation, Biochem. Biophys. Res. Commun. (1988) 153:1251–1256.
Sakuma, I. et al., Identification of Arginine as a Precursor of Endothelium–Derived Relaxing Factor, Proc. Natl. Acad. Sci U.S.A. (1988) 85:8664–8667.
Palmer, R.M.J. et al., Vascular Endothelial Cells Synthesize Nitric Oxide from Arginine, Nature, (1988) vol. 333, 664–666.
Hibbs, J.B. et al., Nitric Oxide: A Cytotoxic Activated Macrophage Effector Molecule, Biochem. Biophys. Res. Commun. (1988) 157:87–94.
Marletta, M.A. et al., Macrophage Oxidation of L–Arginine to Nitrite and Nitrate: Nitric Oxide Is an Intermediate, Biochemistry (1988) 27:8706–8711.
Palmer, R.M.J. et al., Nitric Oxide Release Accounts for the Biological Activity of Endothelium–Derived Relaxing Factor, Nature (1987) 327:524–526.
Stuehr, D.J. et al., Induction of Nitrite/Nitrate Synthesis in Murine Macrophages by BCG Infection, Lymphokines, or Interferon–γ, J. of Immunology (1987) 139:518–525.

(List continued on next page.)

Primary Examiner—Russell Travers (57) ABSTRACT

Guanosine triphosphate pathway tetrahydrobiopterin synthesis antagonist and/or pterin salvage pathway tetrahydrobiopterin synthesis antagonist are administered to inhibit nitric oxide synthesis from arginine in vascular smooth muscle cells in a subject in need of such inhibition (e.g. for prophylactic or curative effect for cytokine–induced hypotension or for restoration of vascular contractile sensitivity to pressor agents in the treatment of such hypotension).

12 Claims, 9 Drawing Sheets

OTHER PUBLICATIONS

Iyengar, R. et al., Macrophage Synthesis of Nitrite, Nitrate and N–Nitrosamines: Precursors and Role of the Respiratory Burst, *Proc. Natl. Acad. Sci. U.S.A.* (1987) vol. 84, 6369–6373.

Turan et al., *Acta Chimica Academiae Scientiarum Hungaricae* (1975) 85:327–332.

Kilbourn et al., $N^G$–Methyl–L–Arginine Inhibits Tumor Necrosis Factor–Induced Hypotension: Implications for the Involvement of Nitric Oxide *Proc. Natl. Acad. Sci. U.S.A.* (1990) 87:3629–3632.

Book of Abstracts, Second International Meeting Biology of Nitric Oxide, cover page, meeting schedule page, abstract headed.

Synthesis of Tetrahydrobiopterin is a Requirement for Induction of Nitric Oxide Synthesis by LPS/Interferon in Vascular Smooth Muscle (Steven S. Gross and Roberto Levi).

Gross, S.S., et al, Biochem.Biophys.Res.Commun,178,No. 3, 823–829(Aug. 15, 1991).

Kaufman,S,et al, J.Biol.Chem.,234,No.10,2683–2688(10/59).

Kaufman,S.,et al, J.Biol.Chem.,242,No. 17,3934–3943(9/67).

Kerler,F.,et al, Exp.Cell Res.,189,151–156(1990).

Kwon,N.S.,et al, J.Biol.Chem.,264,No. 34,20496–20501(12/89).

Milstien,S.,et al, Biochem.Biophys.Res.Commun.,128,No. 3,1099–1107(5/85).

Nichol,C.,et al, Ann.Rev.Biochem.54,729–764(1985).

Tayeh,M.A., et al,J.Biol.Chem.,264,No. 33, 19654–19658(1989).

Werner–Felmayer,G.,et al, J.Exp.Med.,172, 1599–1607(1990).

Ziegler,I.,et al, J.Biol.Chem.,265,No. 28,17026–17030(10/90).

* cited by examiner

BLOCKING INDUCTION OF TETRAHYDROBIOPTERIN TO BLOCK INDUCTION OF NITRIC OXIDE SYNTHESIS

This application is a continuation of application Ser. No. 07/813,507, filed Dec. 26, 1991, now abandoned.

This invention was made at least in part with Government support under Grants HL46403 and HL34215 from the National Institutes of Health.

TECHNICAL FIELD

This invention is directed to a novel method of inhibiting the induction of nitric oxide formation in biological systems by bacterial endotoxins and cytokines.

BACKGROUND OF THE INVENTION

For several decades nitroglycerin has been administered to humans as a vasodilating agent in the treatment of cardiovascular disease. Recently, it has been shown that nitroglycerin so administered is converted in the body to nitric oxide which is the pharmacologically active metabolite. Still more recently, nitric oxide has been shown to be formed enzymatically from arginine as a normal metabolite which is an important component of endothelium-derived relaxing factors (EDRFs). EDRFs are currently being intensively studied as participating in regulation of blood flow and vascular resistance. In addition to vascular endothelium, macrophages have also been shown to produce nitric oxide in the body which is a component of their cell killing and/or cytostatic function.

More recently it has been established that the enzyme forming nitric oxide from arginine, i.e., nitric oxide synthase, occurs in two distinct forms, namely a constitutive form and an inducible form. The constitutive form is present in normal endothelial cells, neurons and some other tissues. Formation of nitric oxide by the constitutive form in endothelial cells is thought to play a role in normal blood pressure regulation. The inducible form of nitric oxide synthase has been found to be present in activated macrophages and is induced in endothelial cells and vascular smooth muscle cells, for example, by various cytokines and/or microbial products. It is thought that in sepsis or cytokine-induced shock, overproduction of nitric oxide by the inducible form of nitric oxide synthase plays an important role in the observed life-threatening hypotension. Furthermore, it is thought that overproduction of nitric oxide by the inducible form of nitric oxide synthase is a basis for insensitivity to clinically used pressor agents such as $\alpha_1$- adrenergic agonists in the treatment of septic or cytokine-induced shock patients.

Considerable research effort has been expended to discover inhibitors for nitric oxide synthase activity. Before the work described herein, said research effort has been directed at uncovering arginine antagonists to function to inhibit nitric oxide synthase activity. A problem with use of the arginine antagonists for this purpose is that the ones uncovered thus far block not only inducible nitric oxide synthase activity but also constitutive nitric oxide synthase activity; and any specificity of inhibition of any particular arginine antagonist for inducible nitric oxide synthase activity is not so high that it is possible to block hypotension-causing, pathological overproduction of nitric oxide (an inducible enzyme-mediated process) to a therapeutically adequate extent (i.e. so that clinically serious hypotension that would normally occur in sepsis or cytokine-induced shock is avoided or so that pressor agent sensitivity is restored), and, at the same time, not block the physiological nitric oxide synthesis which is thought to play a role in neural function and normal blood pressure regulation (constitutive enzyme-mediated processes) and thereby avoid the toxicity (e.g. neuronal toxicity and hypertension) associated with interfering with physiological nitric oxide synthesis.

SUMMARY OF THE INVENTION

The invention herein does not rely on arginine antagonists but rather uses a novel approach to selectively block the induction of nitric oxide synthesis by cytokines and/or microbial products (e.g. bacterial endotoxins) without blocking physiological (constitutive enzyme-mediated) nitric oxide production.

The invention herein draws on the recent discovery that tetrahydrobiopterin is a cofactor in the induction of nitric oxide synthesis (Kwon, N. C., et al, J. Biol. Chem. 264:20496–20501, 1989, and Tayeh, M. A., et al J. Biol Chem. 264:19654–19658, 1989).

The invention herein also draws on the discovery that cytokines, e.g. interferon-gamma, have been found to markedly increase tetrahydrobiopterin levels in various cells including macrophages (Werner, E., et al, Biochem. J 262:861–866, 1989; Kerler, F., et al, Experimental Cell Research 189, 151–156, 1990; Ziegler, I., et al, The Journal of Biological Chemistry, 265, No. 28, 17026–17030, 10/05/90), the discovery in the course of the invention herein that tetrahydrobiopterin synthesis is induced by bacterial endotoxins, the discoveries that tetrahydrobiopterin synthesis occurs via a guanosine triphosphate pathway and via a pterin salvage pathway (Nichol, C., et al, Ann. Rev. Biochem. 54, 729–764, 1985; Milstien, S., et al, Biochem. and Biophys. Res. Comm., 128, No. 3, 1099–1107, 1985; Kaufman, S., et al, J. Biol. Chem., 234, 2683–2688, 10/59; Kaufman, S., J. Biol. Chem., 242, 3934–3943, 9/10/67), and the discovery in the course of the invention that the continuous production of tetrahydrobiopterin, via a guanosine triphosphate pathway or a pterin salvage pathway, is not required for maintaining constitutive nitric oxide synthase activity over at least a period of hours.

It has been discovered herein that inhibiting the synthesis of tetrahydrobiopterin in vascular smooth muscle cells via the guanosine triphosphate pathway and/or the pterin salvage pathway selectively inhibits the induction of nitric oxide synthesis in said cells by bacterial endotoxins and cytokines, i.e. performs such inhibiting without affecting physiological constitutive enzyme-mediated nitric oxide synthesis. The inhibition of nitric oxide synthesis in smooth muscle cells in accordance with the invention is an unexpected result since it has been shown that macrophages which are "normal", ie, are not included for nitric oxide synthesis, already contain enough tetrahydrobiopterin for a maximal rate of nitric oxide synthesis (see Kwon, N. C., et al, J. Biol. Chem. 264:20496–2501, 1989).

In a first embodiment the invention herein is directed at a method of inhibiting induced nitric oxide synthesis from arginine in vascular smooth muscle cells in a subject in need of said inhibition (e.g. for prophylaxis or treatment of systemic hypotension or to restore vascular contractile sensitivity to effects of pressor agents such as $\alpha_1$, adrenergic agents), said method comprising administering to said subject of a nitric oxide synthesis inhibiting therapeutically effective amount of (a) at least one guanosine triphosphate pathway tetrahydrobiopterin synthesis antagonist which is not a reduced pterin that is a substrate for the pterin salvage pathway or (b) at least one pterin salvage pathway tetrahydrobiopterin synthesis antagonist or of both (a) and (b).

In a second embodiment, the invention herein is directed at a method of inhibiting induced nitric oxide synthesis from arginine in vascular smooth muscle cells in a subject in need of said inhibition (e.g. for prophylaxis or treatment of systemic hypotension or to restore vascular contractile sensitivity to effects of pressor agents such as $\alpha_1$, adrenergic agents), said method comprising administering to said subject of nitric oxide synthesis inhibiting therapeutically effective amounts of at least one guanosine triphosphate pathway tetrahydrobiopterin synthesis antagonist which is a reduced pterin that is a substrate for the pterin salvage pathway and of at least one pterin salvage pathway tetrahydrobiopterin synthesis antagonist.

The term "subject" is used herein to mean any mammal, including humans, where nitric oxide formation from arginine occurs. The methods herein for use on subjects contemplate prophylactic use as well as curative use in therapy of an existing condition. When the combination of guanosine triphosphate pathway tetrahydrobiopterin synthesis antagonist and pterin salvage pathway tetrahydrobiopterin synthesis antagonist is used, the amounts used of each should be such that the combination inhibits induced nitric oxide synthesis from arginine.

The guanosine triphosphate pathway (also referred to as the tetrahydropterin pathway) for tetrahydrobiopterin synthesis is described in Nicol, C., et al, Ann. Rev. Biochem. 54, 729–764, 1985. It is considered to comprise the following: Guanosine triphosphate is converted to dihydroneopterin triphosphate in a reaction catalyzed by guanosine triphosphate cyclohydrolase I (GTP CHI; EC 3.5.4.16). In a second step, the dihydroneopterin is converted to an unstable intermediate in a reaction catalyzed by 6-pyruvoyl tetrahydropterin synthase. In a third and fourth step, the unstable intermediate is reduced to tetrahydrobiopterin in reactions mediated by sepiapterin reductase and a possible additional enzyme. GTP CHI is the rate-limiting enzyme for the induced guanosine triphosphate pathway.

The pterin salvage pathway (also referred to as the dihydropterin pathway) for tetrahydrobiopterin synthesis is described in Nicol, C., et al, Ann. Rev. Bioch. 54, 729–764, 1985. The final step of the pterin salvage pathway converts dihydrobiopterin into tetrahydrobiopterin in a reaction catalyzed by dihydrofolate reductase.

Below, LPS is used to mean bacterial lipopolysaccharide endotoxin, IFN is used to mean interferon-gamma, DAHP is used to mean 2,4-diamino-6-hydroxypyrimidine, MTX is used to mean methotrexate and SEP is used to mean sepiapterin.

BRIEF DESCRIPTION OF THE DRAWINGS

FIG. 1 in its main portion depicts the time course of nitrite synthesis in response to LPS (bacterial polysaccharide endotoxin) and interferon-gamma on addition of additives including DAHP (2,4-diamino-6-hydroxypyridine), SEP (sepiapterin) and MTX (methotrexate) and shows the results of Example II.

FIG. 2 in its right-hand portion depicts how the nitrite production response to bacterial lipopolysaccharide and interferon-gamma is affected by methotrexate both alone (CONTROL) and in the presence of sepiapterin and shows results of Example IV.

DETAILED DESCRIPTION

Turning now to the first embodiment described above, the guanosine triphosphate pathway tetrahydrobiopterin synthesis antagonists which are not reduced pterins that are substrates for the pterin salvage pathway include agents selected from the group consisting of guanosine triphosphate cyclohydrolase I inhibitors, 6-pyruvoyl tetrahydrobiopterin synthase inhibitors and sepiapterin reductase inhibitors. The guanosine triphosphate cyclohydrolase I inhibitors include, for example, substituted pyrimidines, oxidized pterins and reduced pterins that are not substrates for the pterin salvage pathway. The substituted pyrimidines include hydroxyl, amino and halogen substituted pyrimidines, for example, 2,4-diamino-6-hydroxypyrimidine, 2,5-diamino-6-hydroxypyrimidine, 4,5-diamino-6-hydroxypyrimidine, 4,5-diaminopyrimidine, and 4,6-diamino-2-hydroxypyrimidine. The oxidized pterins include, for example, neopterin, xanthopterin, isoxanthopterin and biopterin. The reduced pterins that are not substrates for the pterin salvage pathway include, for example, 7,8-dihydro-D-neopterin, (6R,S)-5,6, 7,8-tetrahydro-D-neopterin, dihydrofolic acid and tetrahydrofolic acid. Turning now to the 6-pyruvoyl tetrahydrobiopterin synthase inhibitors, none are currently known. Turning now to the sepiapterin reductase inhibitors, these include N-acetylserotonin.

Turning now to the second embodiment described above, the guanosine triphosphate pathway tetrahydrobiopterin synthesis antagonists which are reduced pterins that are substrates for the pterin salvage pathway are dihydro- or tetrahydropterins. These include, for example, (6R)-5,6,7,8-tetrahydro-L-biopterin, 7,8-dihydro-L-biopterin, and L-sepiapterin.

Turning now to the pterin salvage pathway tetrahydrobiopterin synthesis antagonists, these are the same for the first and second embodiments and are dihydrofolate reductase inhibitors. These include, for example, methotrexate, aminopterin, 10-propargyl-5,8-dideazafolate; 2,4-diamino, 5-(3',4'-dichlorophenyl),6-methylpyrimidine; trimetrexate; pyrimethamine; trimethoprim; pyritrexim 5,10-dideazatetrahydrofolate; and 10-ethyl,10-deaza-aminopterin.

The dosages of the inhibitors for inhibiting vascular dysfunctions resulting from nitric oxide overproduction, e.g. hypotension and pressor hyporesponsivity, generally range from 1 µg/kg to 100 mg/kg with the actual dosage depending on the inhibitor selected. In the case of dihydrofolate reductase inhibitors which are already used clinically, conventional dosages apply. Where required, folates may be administered subsequently to salvage pathway inhibitors to alleviate toxicity in accordance with current usage for cancer chemotherapy or administered concurrently therewith to prevent toxicity arising from folate synthesis inhibition. Preferably the inhibitors are administered intravenously for the specifically aforenamed conditions because of the need for fast response. For other conditions where induced nitric oxide synthesis may be detrimental, e.g. in immune-rejection phenomena and neurodegenerative diseases, other methods of administration may also be appropriate, e.g. oral, subcutaneous, or intramuscular methods of administration.

The following examples are illustrative of the concepts of the invention and represent the best mode known to the inventor at this time.

EXAMPLE I

Aortic smooth muscle cells were cultured by explanting segments of the medial layer of aortae from adult male Fischer 344 rats. Aortae were removed aseptically and freed of adventitial and endothelial cells by scraping both the lumenal and abluminal surfaces. Medial fragments (1–2 mm) were allowed to attach to dry Primaria 25 cm² tissue culture flasks (Falcon; Oxnard, Calif.) which were kept moist with growth medium until cells emerged. Cultures were fed twice weekly with medium 199 containing 10% fetal bovine serum, 25 mM HEPES, 2 mM L-glutamine, 40 µg/ml endothelial cell growth supplement (Biomedical Technologies; Stoughton, Mass.) and 10 µg/ml gentamycin (GIBCO; Grand Island, N.Y.). When primary cultures became confluent, they were passaged by trypsinization and the explants were discarded. Cells in passage 10–15 were seeded at 20,000/well.

When the cells became confluent (density of 60–80×10³ cells in a well), the medium was removed by suction and fresh medium consisting of 200 µl of RPMI 1640 (Whittaker Laboratories) containing 10% bovine calf serum, 2.5 mM glutamine and penicillin (80 U/ml), streptomycin (80 µg/ml) and fugizone (2 µg/ml) was added to each well via a pipette.

Groups of 4 wells were each administered fixed concentrations of 2,4-diamino-6-hydroxypyrimidine (DAHP), namely 30 µg/ml, 100 µg/ml, 300 µg/ml, 1000 µg/ml and 3000 µg/ml, and a control was provided of wells which received no DAHP. To each was also added bacterial lipopolysaccharide (endotoxin; Serotype: E. Coli. 0111:B4, 50 µg/ml) plus rat interferon-gamma (50 ng/ml). The wells were then incubated at 37° C. in a humidified incubator for 24 hours. After this time, nitrite accumulation in the cell culture media was measured. Nitrite was measured by adding 100 µl of cell culture medium to 100 µl of Greiss reagent (0.5% sulfanilamide and 0.05% naphthylethylenediamine dihydrochloride in 2.5% phosphoric acid) and $OD_{550}$nm (optical density at 550 nm) was immediately measured using a microplate reader (Molecular Devices; Menlo Park, Calif.). Nitrite concentrations were determined by comparison with standard solutions of sodium nitrite prepared in culture medium. Background nitrite levels in smooth muscle cell cultures not exposed to cytokines were subtracted from experimental values.

Figure 1:
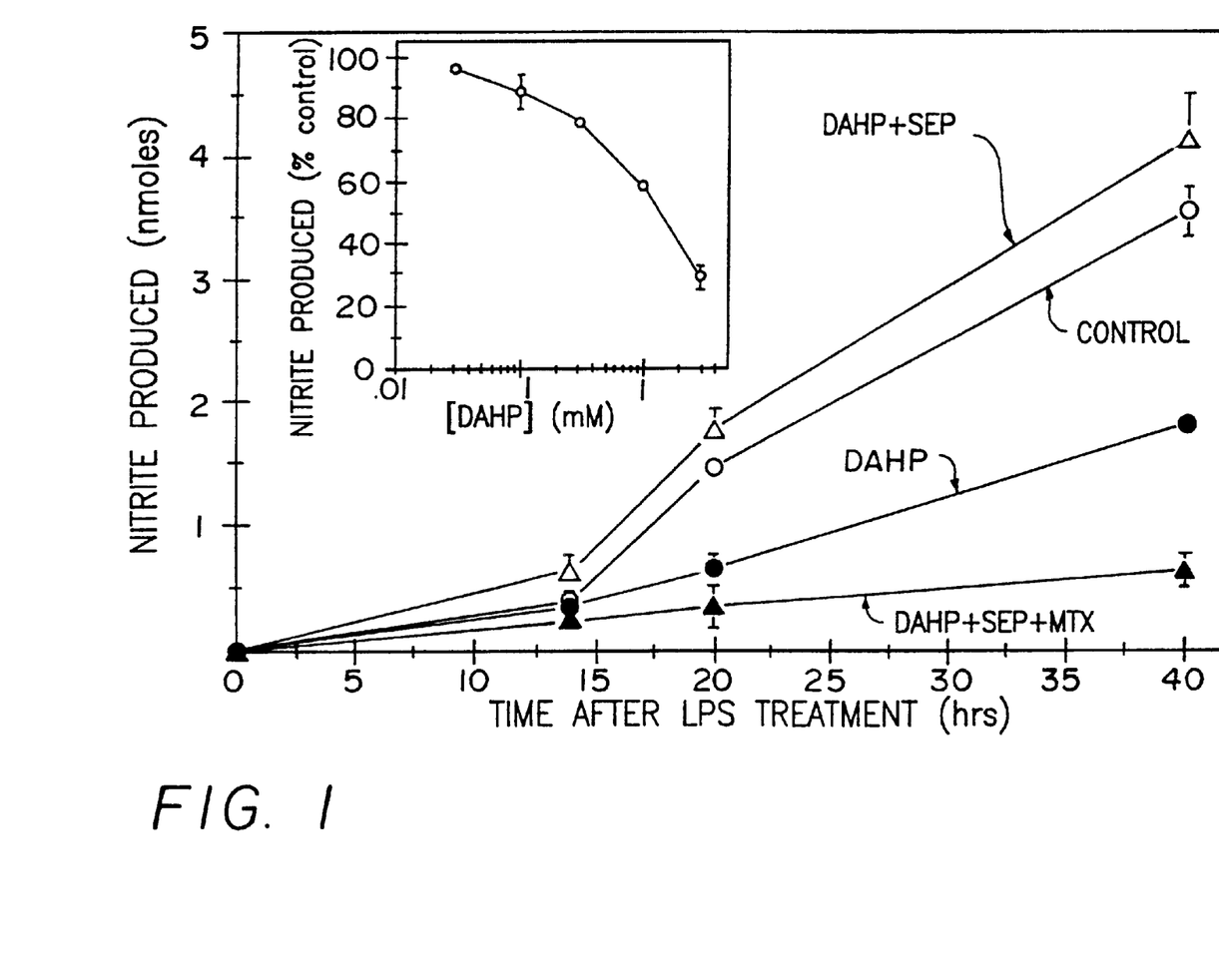
FIG. 1 in its inset portion is a graph depicting a concentration-response relationship for inhibition by DAHP (2,4-diamino-6-hydroxypyrimidine) of 24-hr. nitrite accumulation in a cell culture medium of rat aortic smooth muscle cells which are induced by bacterial lipopolysaccharide/interferon-gamma and depicts the results of Example I.

Nitrite production is shown in the inset to FIG. 1. The results show that increasing concentrations of DAHP progressively inhibit nitrite production. Separate experiments (not explained here) showed that nitrite production is a direct indicator of nitric oxide synthesis. Thus, this experiment shows that DAHP inhibits nitric oxide production.

EXAMPLE II

Example I was repeated except samples of cell culture media were collected at 14 hours, 20 hours and 40 hours. The cells were incubated with 2 mM DAHP or no DAHP (4 replicates for each time). The results are shown in the main figure of FIG. 1 in the curves denoted CONTROL and DAHP. The results showed that the DAHP reduced the release of nitric oxide over time.

In another case the DAHP was added together with 100 µm sepiapterin (SEP). The results are shown in the curve in the main figure of FIG. 1 in the curve denoted DAHP+SEP. The results show that sepiapterin overcame the blockade of nitric oxide synthesis caused by DAHP. This indicates that the mechanism of DAHP inhibition is specifically by blocking tetrahydrobiopterin synthesis from guanosine triphosphate since it is known that sepiapterin can form tetrahydrobiopterin by the alternate pterin salvage pathway.

In another case methotrexate (10 µM) was added together with the DAHP and sepiapterin. The results are shown in FIG. 1 in the curve denoted DAHP+SEP+MTX. The results show that sepiapterin was unable to overcome the inhibition of nitric oxide synthesis caused by DAHP. Since methotrexate is well known to be a potent and selective inhibitor of dihydrofolate reductase, and therefore blocks the pterin salvage pathway, this result indicates that blocking both pathways for tetrahydrobiopterin synthesis completely eliminates the induction of nitric oxide synthesis in smooth muscle cells by the combination of endotoxin and cytokine.

EXAMPLE III

Figure 2:
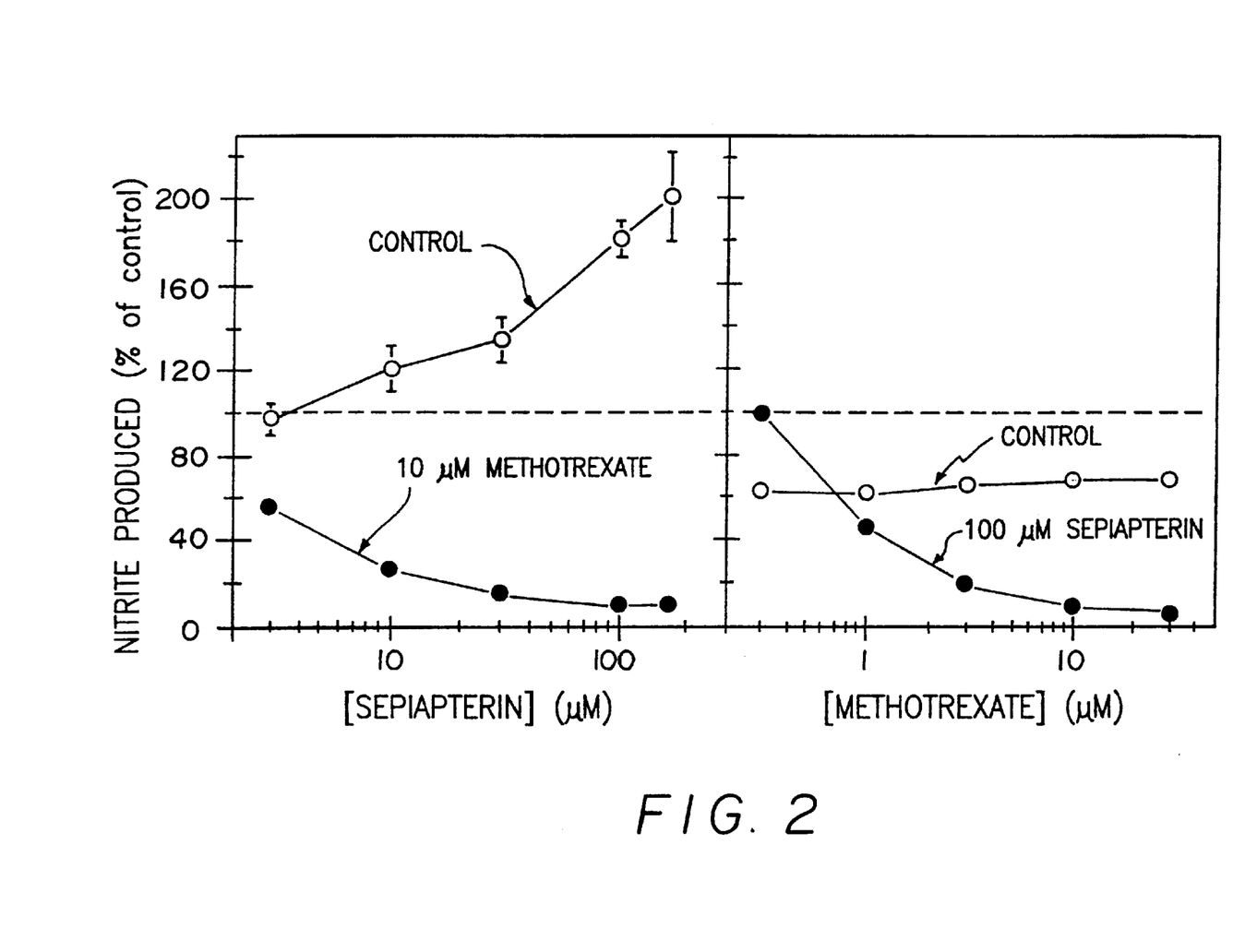
FIG. 2 in its left-hand portion depicts how the nitrite production response of rat aortic smooth muscle cells to bacterial lipopolysaccharide and interferon gamma is affected by sepiapterin both alone (CONTROL) and in the presence of methotrexate and shows results of Example III.

An experiment was carried out the same as in Example I except that sepiapterin was added instead of DAHP, in concentrations of 3, 10, 30, 100 and 300 µM, in the presence or absence (control) of 10 µM methotrexate. The results are shown on the left hand panel of FIG. 2. The results show that sepiapterin causes an increase of induced nitric oxide production. Since sepiapterin directly forms tetrahydrobiopterin in the pterin salvage pathway, this indicates that tetrahydrobiopterin is rate limiting for nitric oxide synthesis in vascular smooth muscle cells. In contrast, when methotrexate was present, sepiapterin completely inhibited induced nitric oxide synthesis. This indicates that when the pterin salvage pathway is blocked (by the methotrexate), the sepiapterin functions as a GTP CHI inhibitor to block the guanosine triphosphate pathway and that when both pathways for tetrahydrobiopterin synthesis are blocked, induced nitric oxide synthesis does not occur.

EXAMPLE IV

An experiment was carried out the same as in Example I except that methotrexate was added instead of DAHP in concentrations of 0.3, 1, 3, 10 and 30 $\mu$M, in the presence or absence (control) of 100 $\mu$M sepiapterin. The results are shown on the right hand side of FIG. 2. The results show that maximally effective concentrations of methotrexate inhibit 30–40% of induced nitric oxide synthesis, and that, when sepiapterin is present, methotrexate completely inhibits induced nitric oxide synthesis, indicating that sepiapterin blocks the guanosine triphosphate pathway and that when both pathways for tetrohydrobiopterin synthesis are blocked, induced nitric oxide synthesis in vascular smooth muscle cells does not occur.

EXAMPLE V

Figure 3:
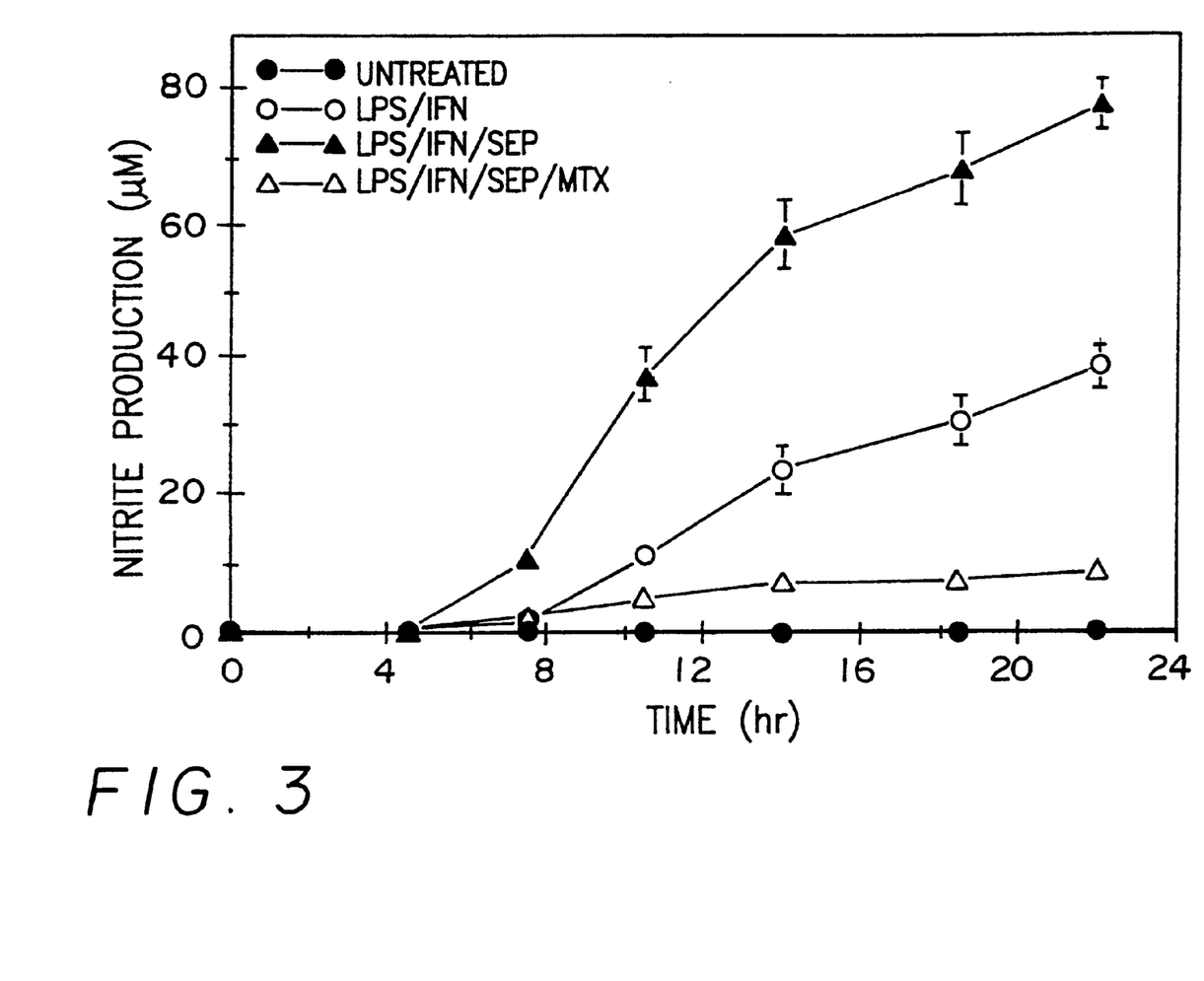
FIG. 3 depicts a time course of LPS (bacterial lipopolysaccharide) and IFN (interferon-gamma) induced nitrite synthesis of rat aortic smooth muscle cells and how it is affected by SEP (sepiapterin) both alone and in the presence of MTX (methotrexate) and shows results of Example V.

An experiment was carried out to study the time course of induced nitric oxide synthesis. Nitric oxide synthesis was induced by bacterial lipopolysaccharide and rat interferon-gamma as in Example I. Nitric oxide synthesis commenced after a delay of about 8 hours. When the same experiment was performed in the presence of 100 $\mu$M sepiapterin, nitric oxide production commenced much earlier and was increased in amount at all times studied indicating that the availability of tetrahydrobiopterin is rate limiting for the onset and degree of induced nitric oxide production. Methotrexate (used in 10 $\mu$M concentration) in combination with sepiapterin caused a near complete inhibition of induced nitric oxide synthesis consistent with results of previous examples. The results of this experiment are depicted in FIG. 3.

EXAMPLE VI

An experiment is carried out the same as in Example I except that tetrahydrobiopterin is added instead of DAHP, in concentrations of 3, 10, 30, 100 and 300 $\mu$M in the presence or absence (control) of 10 $\mu$M methotrexate. The results are that tetrahydrobiopterin alone causes a small increase in induced nitric oxide synthesis. However, when methotrexate is present, tetrahydrobiopterin inhibits induced nitric oxide synthesis, indicating that tetrahydrobiopterin does not enter cells directly and is first oxidized and further that the tetrahydrobiopterin inhibits the guanosine triphosphate pathway of vascular smooth muscle cells.

EXAMPLE VII

Figure 4:
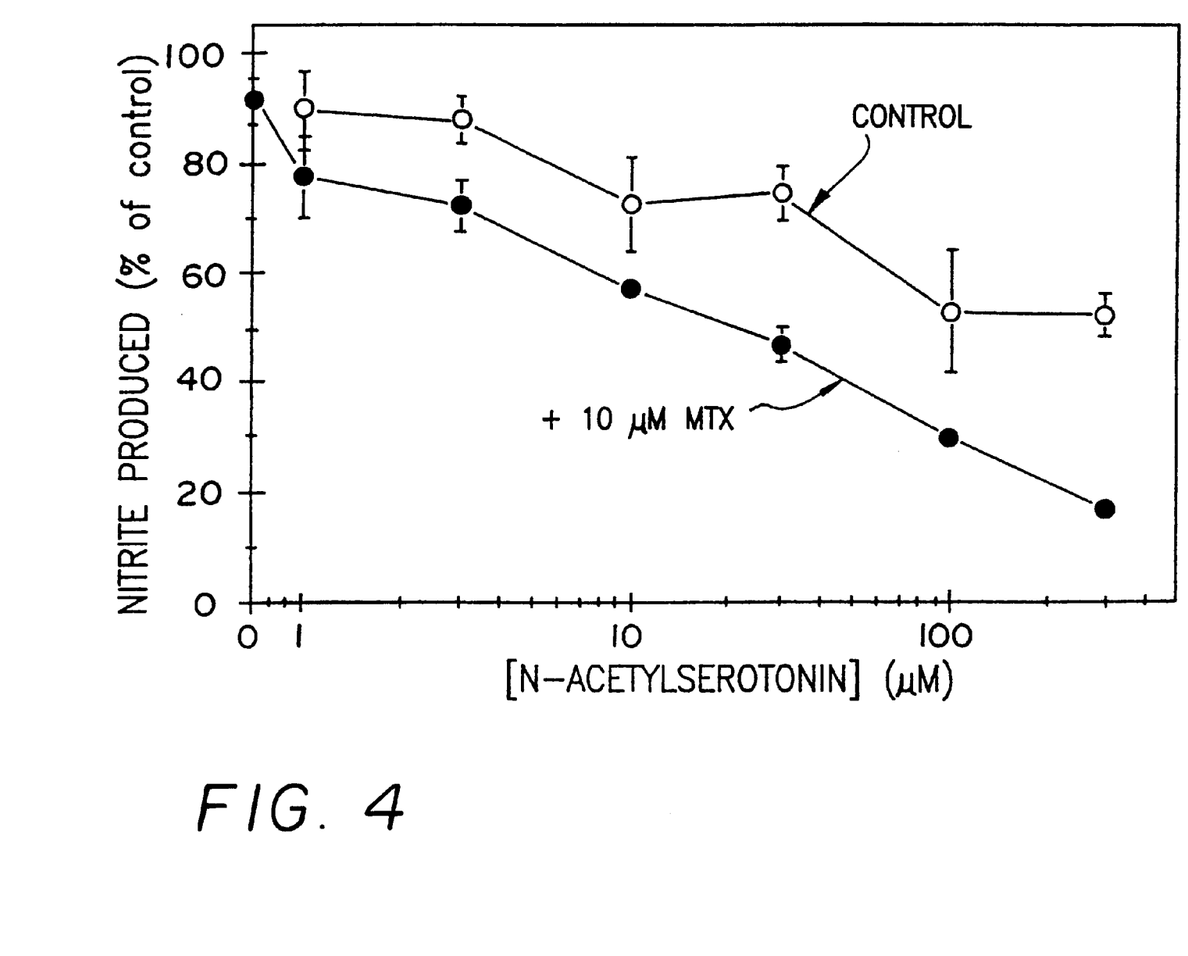
FIG. 4 depicts how the nitrite production response of rat aortic smooth muscle cells to bacterial lipopolipaccharide and interferon-gamma is affected by N-acetylserotonin both alone (CONTROL) and in the presence of MTX (methotrexate) and shows results of Example VII.

An experiment was carried out the same as in Example I except that N-acetylserotonin was used instead of DAHP, at concentrations of 1, 3, 10, 30, 100 and 300 $\mu$M, in the presence or absence (control) of 10 $\mu$M methotrexate. The results are shown in FIG. 4. The results show that when N-acetylserotonin is given alone, the induced nitric oxide synthesis is inhibited maximally by approximately 50%. However, when methotrexate was present, a near complete inhibition is shown. This demonstrates that N-acetylserotonin blocks the guanosine tryphosphate pathway and that inhibition of both pathways of tetrahyrobiopterin synthesis is necessary for maximal nitric oxide synthesis inhibition.

EXAMPLE VIII

Rat aortic smooth muscle cells are prepared as in Example I except that they are grown to confluence in 75 cm$^2$ tissue culture flasks.

Figure 5:
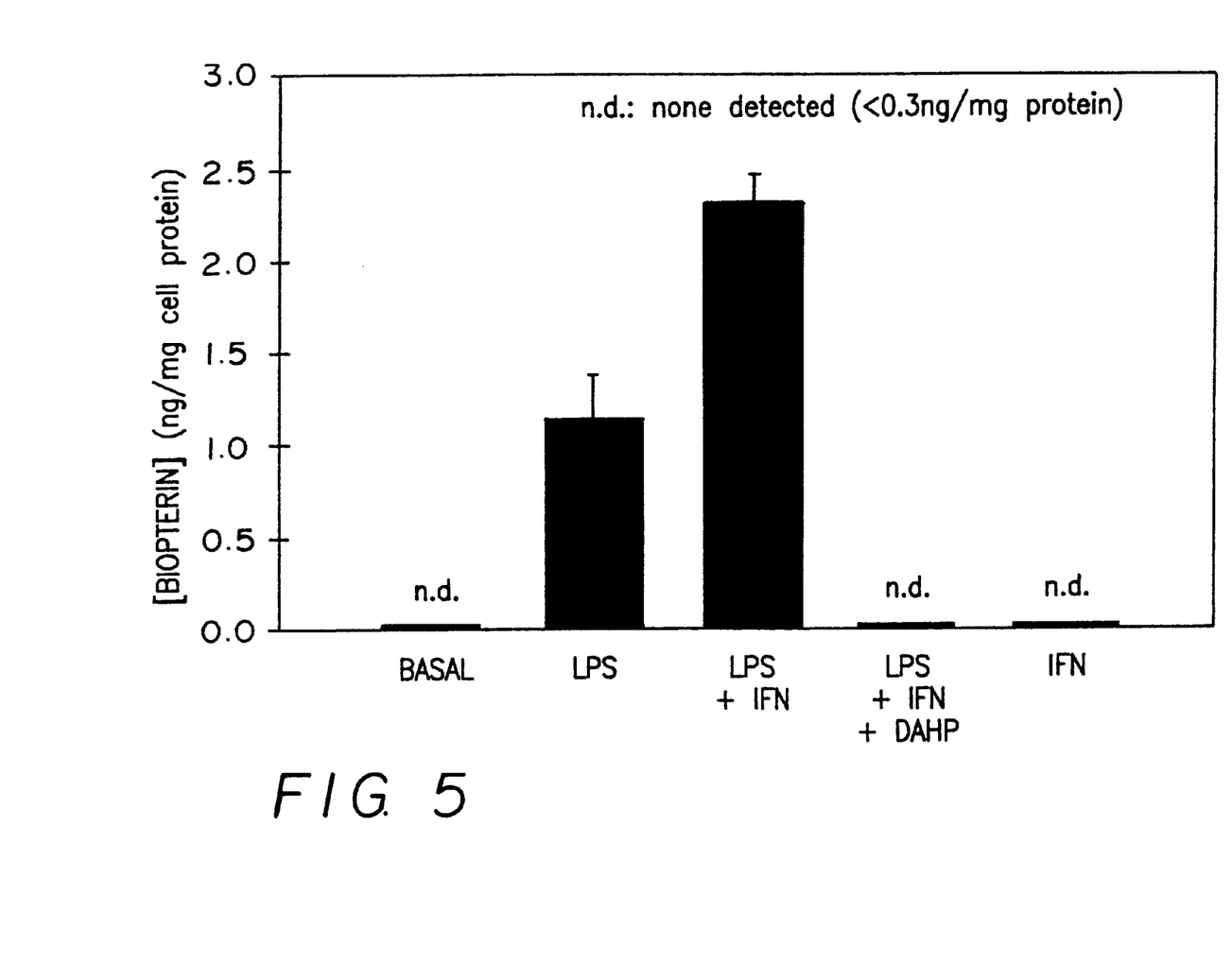
FIG. 5 depicts the biopterin content of smooth muscle cells under basal conditions and after treatment for 12 hours with various additives including LPS (bacterial lipopolysaccharide), IFN (interferon-gamma), and DAHP (2,4-diamino-6-hydroxypyrimidine) and shows results of Example VIII.

Groups of flasks (6 to a group) were treated with no additive (BASAL), bacterial lipopolysaccharide (LPS) as in Example I, LPS as in Example I and interferon-gamma (IFN) as in Example I, LPS and IFN as in Example I and DAPH (3 mM) and IFN (as in Example I) alone. After 12 hours incubation in a humidified incubator at 37° C., cells were harvested with a Teflon cell scraper, lysed by three cycles of freezing and thawing in liquid nitrogen and a 37° C. water bath. The cell lysate was centrifuged at 12000 RPM in a Beckman Microfuge. The supernatants were recovered and acidified with 1N HCl, and the pterins present were oxidized by addition of KI/I$_2$ solution (1% I$_2$, 2% KI in 1N HCl), and incubated at 37° C. for 1 hour in the dark. Excess I$_2$ was removed by treatment with 0.1 M ascorbic acid. Samples were made pH 7.8 with 1N NaOH and 200 mM TRIS buffer and subjected to HPLC analysis for total biopterin content using a reverse phase C$_{18}$ column (Beckman, 3 micron) and fluorescence detection with excitation at 356 nm and emission at 445 nm. The results are shown in FIG. 5. As shown FIG. 5, untreated smooth muscle cells and interferon-treated smooth muscle cells do not have detectable levels of biopterin. However as indicated in FIG. 5, endotoxin (LPS) treated smooth muscle cells contain significant amounts of biopterin and this biopterin content was further increased by interferon (IFN). Most importantly as indicated in FIG. 5, DAHP completely abolished the increase in cellular biopterin caused by LPS and IFN.

EXAMPLE IX

Figure 6:
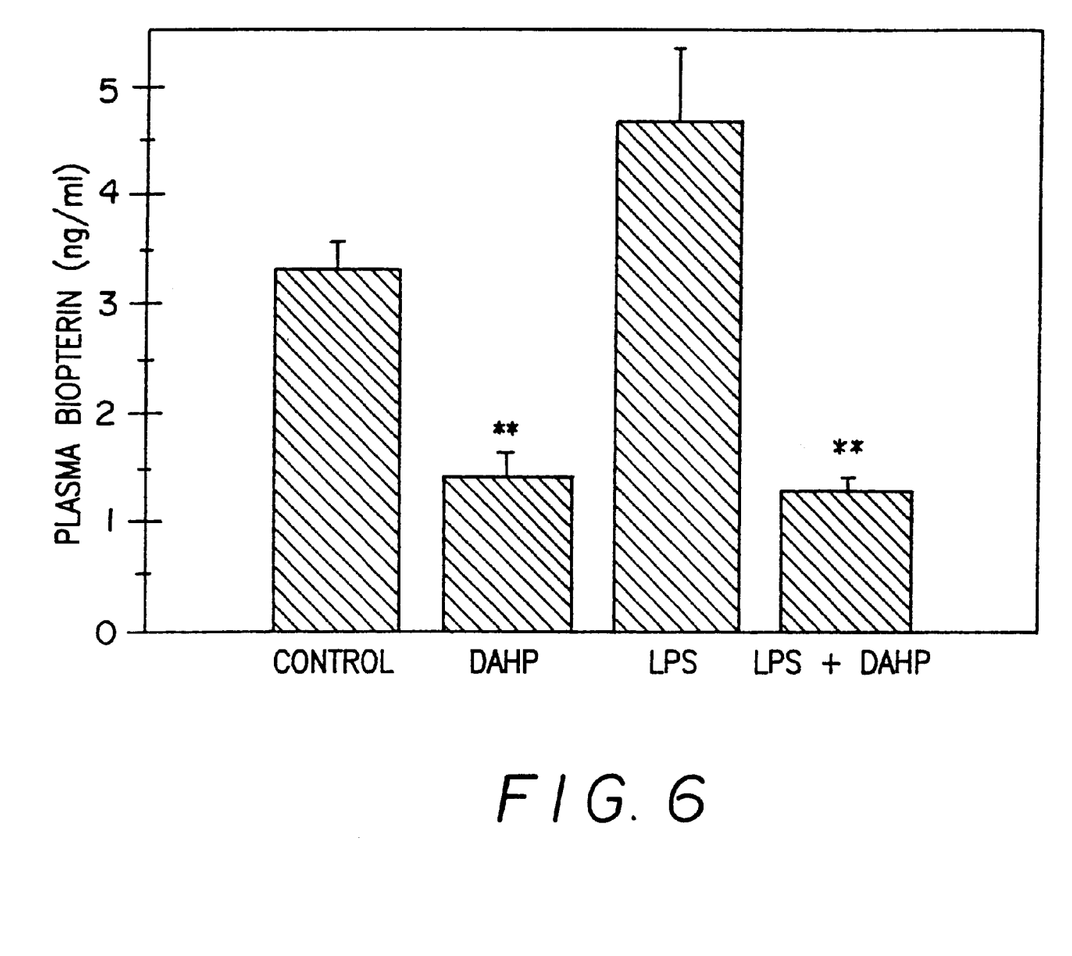
FIG. 6 depicts plasma biopterin levels in rats and how they are affected by agents including DAHP (2,4-diamino-6-hydroxypyrimidine) and LPS (bacterial lipopolysaccharide endotoxin) and shows results of Example IX. The asterisks above an error bar indicate a statistically significant reduction in biopterin (relative to control) with $p<0.01$ determined by student's t-test.

Groups of 6 to 20 Sprague-Dawley rats (250–300 g) were injected with no agent (control), DAHP (1 g/kg intraperitonially), LPS 15 mg/kg, i.p.) and the DAHP and LPS. After 6 hours, animals were anesthetized with ether and blood was drawn by cardiac puncture. Plasma was obtained by centrifugation and total biopterin levels were measured as in Example VIII. The results are shown in FIG. 6. As shown in FIG. 6, DAHP reduced the control concentration of plasma biopterin by greater than 50% and completely abolished the elevated plasma biopterin concentration caused by LPS. This shows that DAHP is effective in vivo in blocking tetrahydrobiopterin synthesis.

EXAMPLE X

Figure 7:
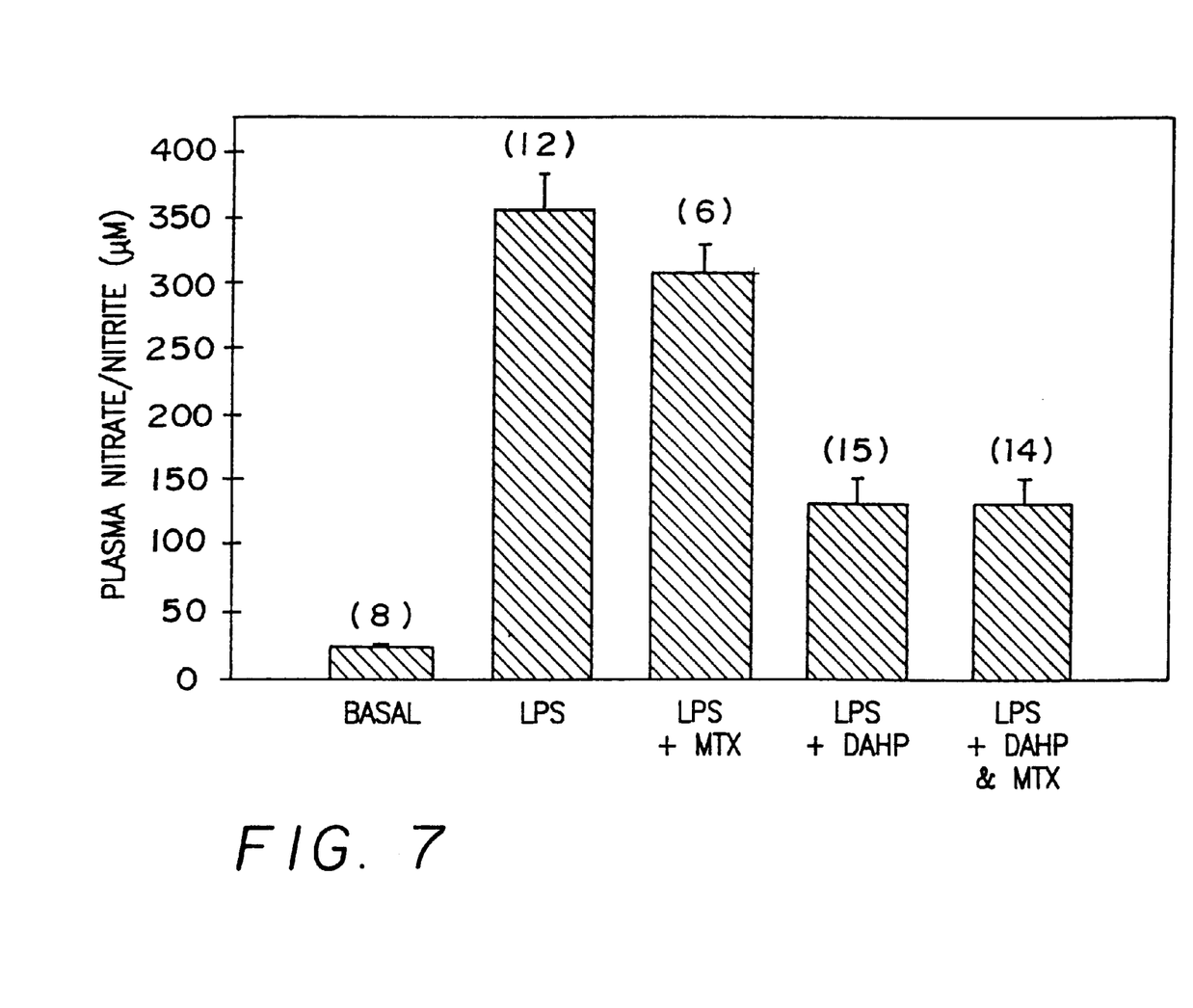
FIG. 7 depicts plasma nitrate/nitrite levels in rats and how they are affected by agents including LPS (bacterial lipopolysaccharide endotoxin), MTX (methotrexate) and DAHP (2,4 -diamino-6-hydroxypyrimidine) and shows results of Example X. The numbers in parentheses indicate the number of rats for the determination.

Groups of 6 to 15 Sprague-Dawley rats (250–300 g) were injected i.p. with no agents (BASAL), LPS (15 mg/kg), LPS at 15 mg/kg plus methotrexate (MTX) at 10 mg/kg, LPS (15 mg/kg) plus DAHP (1 g/kg) and LPS (15 mg/kg) plus DAHP (1 g/kg) plus MTX (10 mg/kg). After 6 hours blood was drawn by cardiac puncture. Plasma was obtained by centrifugation and the total of nitrate and nitrite concentration was measured by an automated colorimetric assay. In the assay, an automatic sample injector was used to apply samples to a copper-coated cadmium column for catalytic reduction of nitrate to nitrite. Samples were then mixed on-line with a stream of buffer-containing (10 g/ml sulfanilamide, 1 g/ml naphthalenediamine and 5% ortho-phosphoric acid). Nitrate/nitrite concentration was measured based on optical density (O.D.) at 546 nm using authentic nitrite as a referece standard. The results are shown in FIG. 7. As indicated in FIG. 7, LPS caused a 28-fold increase in serum nitrate/nitrite, this was slightly reduced by methotrexate but markedly reduced by DAHP in the absence or presence of methotrexate. This demonstrates that DAHP is an effective inhibitor of LPS-induced nitric oxide production in vivo.

EXAMPLE XI

Figure 8:
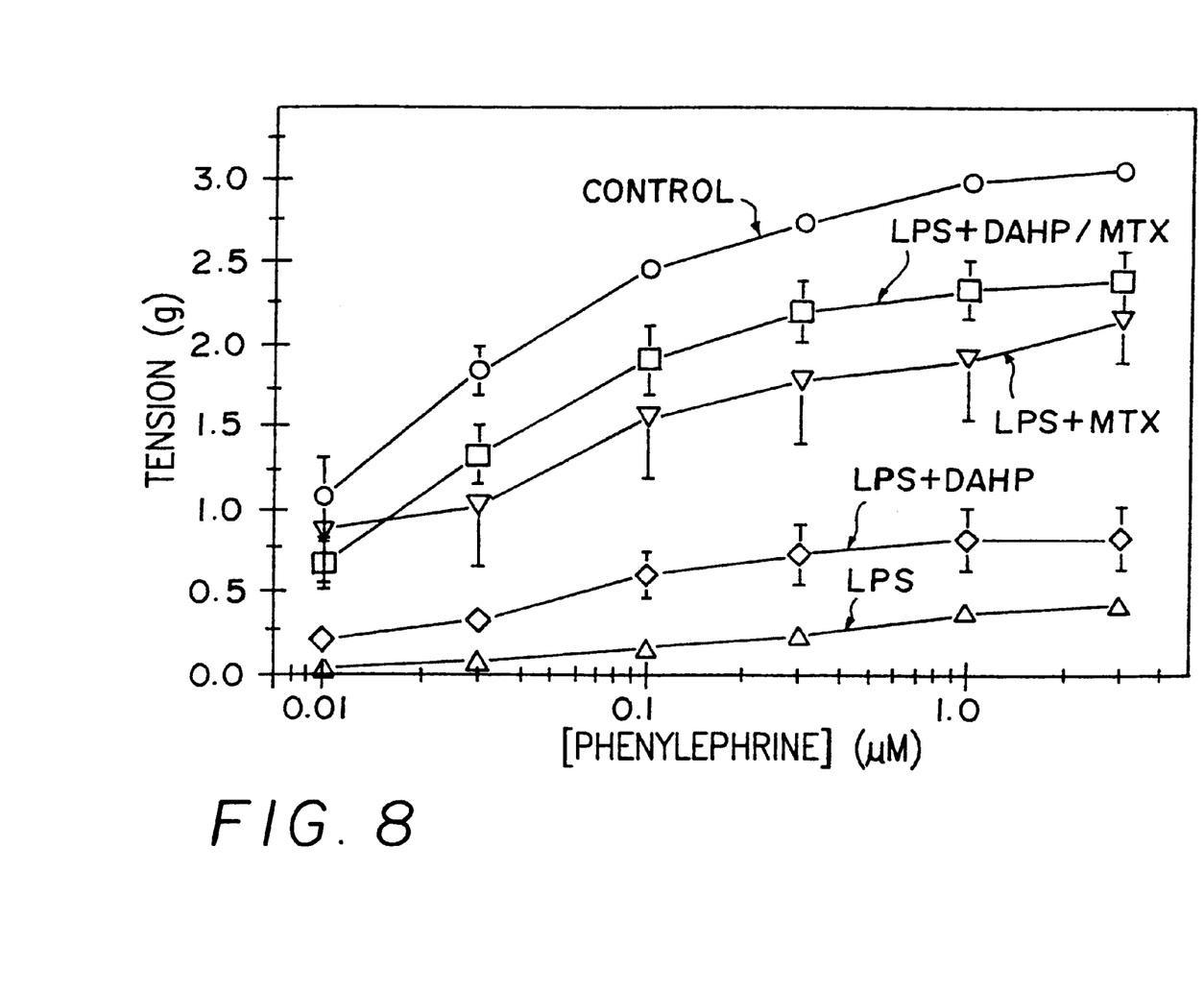
FIG. 8 depicts phenylephrine induced constrictory responses of isolated aortic rings prepared from rats that have been pretreated with agents including LPS (bacterial lipopolysaccharide endotoxin), MTX (methotrexate) and DAPH (2,4-diamino-6-hydroxypyrimidine) and shows results of Example XI.

Groups of rats (6–10 per group) were either untreated, i.p. injected with LPS (15 mg/kg), i.p. injected with the LPS plus DAHP (1 g/kg), i.p. injected with the LPS plus MTX (10 mg/kg), and i.p. injected with the combination of the LPS, the DAHP and the MTX. After 6 hours, the rats were sacrificed and their thoracic aortae were removed and immersed in oxygenated Kreb's solution at 37° C. The Kreb's solution had the following composition in mM: NaCl, 110; KCl, 4.8; $CaCl_2$, 2.5, $KH_2PO_4$, 1.2; $NaHCO_3$, 25; and dextrose, 11. Two to three mm wide rings were cut from the aortae and placed in an oxygenated organ bath under 2 gm of tension. After a 1 hour equilibration, contractile response to phenylephrine were determined by cumulative dose response analysis. The results are shown in FIG. 8. As indicated in FIG. 8, LPS almost completely eliminated the constrictor response caused by the $\alpha_1$ adrenergic agonist phenylephrine, DAHP slightly overcame this inhibition by LPS of phenylephrine response, whereas MTX markedly restored phenyephrine sensitivity and the combination of DAHP and MTX was more effective than either agent alone. This shows that tetrahydrobiopterin synthesis inhibitors can block in vivo nitric oxide production and thereby restore vascular contractile sensitivity to pressor drugs.

EXAMPLE XII

Figure 9:
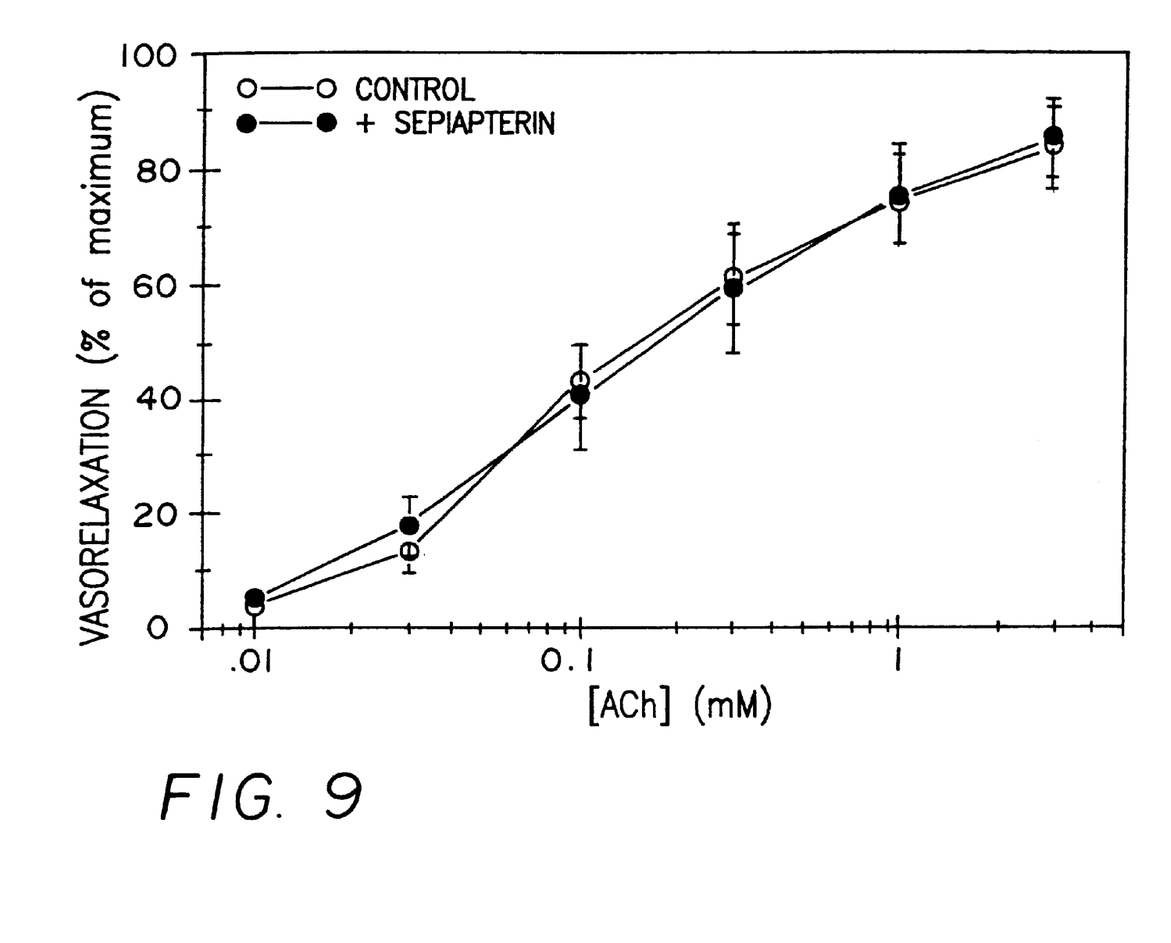
FIG. 9 depicts vasodilatory responses of isolated rat aortic rings to ACh (acetylcholine) before (CONTROL) and after treatment with sepiapterin.

As in Example XI rats were sacrificed and thoracic aortae isolated and rings were prepared in organ baths for tension recording. The rings were preconstricted with phenylephrine (0.3 $\mu$M) and relaxation was measured upon progressive and cumulative addition of acetylcholine (ACh) to the organ baths. Experiments were performed using 4 to 8 replicate rings before, and 30 minutes after exposure to sepiapterin (100 $\mu$M). The results are shown in FIG. 9. As indicated in FIG. 9, the sepiapterin did not at all inhibit the ability of acetylcholine to cause vosorelaxation. This indicates that constitutive nitric oxide synthase which is present in endothelial cells is not limited by tetrahydrobiopterin availability. When methotrexate (10 $\mu$M) is substituted for the sepiapterin, the same results are obtained. Thus, de novo synthesis (guanosine triphosphate pathway synthesis) of tetrahydrobiopterin is not required to maintain constitutive nitric oxide synthesis in endothelial cells over at least several hours.

When in the above examples, N-acetylserotonin replaces DAHP, in vivo results similar to what are obtained with DAPH, can be obtained.

When in the above examples, other pyrimidines, e.g. 2,5-diamino-6-hydroxypyrimidine, 2,4-diamino-6-hydroxypyrimidine or 4,6-diamino-2-hydroxypyrimidine, replace DAHP, similar guanosine triphosphate passageway blocking results are obtained.

When the above examples, other pterins replace sepiapterin, especially reduced pterins, e.g. (6R)-5,6,7,8-tetrahydro-L-biopterin or 7,8-dihydro-L-biopterin or 7,8-dihydro-D-neopterin, or 5,6,7,8-tetrahydro-D-neopterin or dihydrofolic acid or tetrahydrofolic acid or D,L-6-methyl-5,6,7,8-tetrahydropterin or 2-amino-6,7-dimethyl-4-hydroxy-5,6,7,8-tetrahydropteridine, similar guanosine triphosphate passageway blocking results are obtained and in some cases the reduced pterins also act as substrates for the pterin salvage pathway.

When in the above examples, other dihydrofolate reductase inhibitors replace methotrexate, e.g. aminopterin or 10-propargyl-5,8-dideazafolate or 2,4-diamino,5-(3',4'-dichlorophenyl),6-methylpyrimidine trimetrexate, or pyrimethamine or trimethoprim or pyritrexim 5,10-dideazatetrahydrofolate or 10-ethyl,10-deaza-aminopterin, similar results of pterin salvage pathway blocking are obtained.

When other pressor agents are substituted for phenylephrine in Example XI, e.g. angiotensin II, norepinephrine or thromboxane analogs (i.e. u46619) similar results are obtained to those obtained in Example XI.

Many variations of the above will be obvious to those skilled in the art. Thus, the invention is defined by claims.

What is claimed is:

1. A method of prophylaxis or treatment of a subject for systemic hypotension caused by pathological overproduction of nitric oxide from arginine induced in vascular smooth muscle cells in said subject by therapy of said subject with a cytokine, said method comprising administering to said subject of a therapeutically effective amount of (a) at least one guanosine triphosphate pathway tetrahydrobiopterin synthesis antagonist which is not a reduced pterin that is a substrate for the pterin salvage pathway or (b) at least one dihydrofolate reductase inhibitor or both (a) and (b), thereby to inhibit nitric oxide synthesis in said cells to ameliorate said hypotension.

2. The method of claim 1, which comprises administering to said subject of (a) but not (b).

3. The method of claim 1, which comprises administering to said subject of (b) but not (a).

4. The method of claim 1, which comprises administering to said subject of (a) and (b).

5. A method of prophylaxis or treatment of a subject for systemic hypotension caused by pathological overproduction of nitric oxide from arginine induced in vascular smooth muscle cells in said subject by therapy of said subject with a cytokine, said method comprising administering to said subject of therapeutically effective amounts of at least one guanosine triphosphate pathway tetrahydrobiopterin synthesis antagonist which is a reduced pterin that is a substrate for the pterin salvage pathway and of at least one dihydrofolate reductase inhibitor, thereby to inhibit nitric oxide synthesis in said cells to ameliorate said hypotension, said guanosine triphosphate pathway tetrahydrobiopterin synthesis antagonist which is a reduced pterin that is a substrate for the pterin salvage pathway being selected from the group consisting of 7,8-dihydro-L-biopterin and L-sepiapterin.

6. A method of treatment of a subject for systemic hypotension or expected systemic hypotension caused by pathological overproduction of nitric oxide from arginine induced in vascular smooth muscle cells in said subject by bacterial endotoxins, said method comprising administering to said subject of a therapeutically effective amount of (a) at least one guanosine triphosphate pathway tetrahydrobiopterin synthesis antagonist which is not a reduced pterin that is a substrate for the pterin salvage pathway or (b) at least one dihydrofolate reductase inhibitor or both (a) and (b), thereby to inhibit nitric oxide synthesis in said cells to ameliorate said hypotension.

7. The method of claim 6, which comprises administering to said subject of (a) but not (b).

8. The method of claim 6, which comprises administering to said subject of (b) but not (a).

9. The method of claim 6, which comprises administering to said subject of (a) and (b).

10. A method of treatment of a subject for systemic hypotension or expected systemic hypotension caused by pathological overproduction of nitric oxide from arginine induced in vascular smooth muscle cells in said subject by bacterial endotoxins, said method comprising administering to said subject of therapeutically effective amounts of at least one guanosine triphosphate pathway tetrahydrobiopterin synthesis antagonist which is a reduced pterin that is a substrate for the pterin salvage pathway and of at least one dihydrofolate reductase inhibitor, thereby to inhibit nitric oxide synthesis in said cells to ameliorate said hypotension, said guanosine triphosphate pathway tetrahydrobiopterin synthesis antagonist which is a reduced pterin that is a substrate for the pterin salvage pathway being selected from the group consisting of 7,8-dihydro-L-biopterin and L-sepiapterin.

11. The method of claim 1 wherein the antagonist of (a) is selected from the group consisting of guanosine triphosphate cyclohydrolase I inhibitors and sepiapterin reductase inhibitors.

12. The method of claim 6 wherein the antagonist of (a) is selected from the group consisting of guanosine triphosphate cyclohydrolase I inhibitors and sepiapterin reductase inhibitors.

* * * * *

UNITED STATES PATENT AND TRADEMARK OFFICE
CERTIFICATE OF CORRECTION

PATENT NO. : 6,274,581 B1
APPLICATION NO. : 08/063067
DATED : August 14, 2001
INVENTOR(S) : Steven S. Gross It is certified that error appears in the above-identified patent and that said Letters Patent is hereby corrected as shown below:

In column 1, lines 7-9, replace:

"This invention was made at least in part with Government support under Grants HL46403 and HL34215 from the National Institutes of Health."

with:

-- This invention was made with Government support under Contract Numbers HL46403 and HL34215 from the National Institutes of Health --.

Signed and Sealed this

Thirtieth Day of September, 2008

JON W. DUDAS
*Director of the United States Patent and Trademark Office*